(12) United States Patent
Qiao et al.

(10) Patent No.: US 12,414,720 B2
(45) Date of Patent: Sep. 16, 2025

(54) IMPLANTABLE MEDICAL DEVICES, SYSTEMS AND METHODS FOR REDUCING T-WAVE OVERSENSING AND ARRHYTHMIA UNDERSENSING

(71) Applicant: Pacesetter, Inc., Sylmar, CA (US)

(72) Inventors: Yun Qiao, Sunnyvale, CA (US); Nima Badie, Oakland, CA (US); Wenwen Li, Studio City, CA (US); Chaoyi Kang, Northridge, CA (US); Jan Mangual, Milan (IT); Fady Dawoud, Studio City, CA (US)

(73) Assignee: Pacesetter, Inc., Sylmar, CA (US)

( * ) Notice: Subject to any disclaimer, the term of this patent is extended or adjusted under 35 U.S.C. 154(b) by 600 days.

(21) Appl. No.: 17/744,217

(22) Filed: May 13, 2022

(65) Prior Publication Data
US 2023/0121674 A1 Apr. 20, 2023

Related U.S. Application Data

(60) Provisional application No. 63/262,778, filed on Oct. 20, 2021.

(51) Int. Cl.
*A61B 5/29* (2021.01)
*A61B 5/33* (2021.01)
(Continued)

(52) U.S. Cl.
CPC ............ *A61B 5/29* (2021.01); *A61B 5/33* (2021.01); *A61B 5/335* (2021.01); *A61B 5/352* (2021.01);
(Continued)

(58) Field of Classification Search
CPC .. A61B 5/29; A61B 5/33; A61B 5/335; A61B 5/352; A61B 5/355; A61B 5/361;
(Continued)

(56) References Cited

U.S. PATENT DOCUMENTS 6,671,548 B1 12/2003 Mouchawar et al.
8,914,106 B2 12/2014 Charlton et al.
(Continued)

FOREIGN PATENT DOCUMENTS

EP 3209376 A1 8/2017
EP 3383486 A1 10/2018

OTHER PUBLICATIONS

"Spontaneous T-wave oversensing," Cardiocases, Pacing & Defibrillation, ICT in 20 clinical situations, downloaded on Apr. 22, 2022, [https://www.cardiocases.com/en/pacingdefibrillation/clinical-situation/icd/spontaneous-t-wave-oversensing], 9 pages.
(Continued)

*Primary Examiner* — James M Kish
*Assistant Examiner* — Natasha Patel
(74) *Attorney, Agent, or Firm* — Pearl Cohen Zedek Latzer Baratz LLP

(57) ABSTRACT

Described herein are implantable medical devices and systems, and methods for use therewith, for reducing T-wave oversensing and arrhythmia undersensing that occur due to inappropriate filtering of a signal indicative of cardiac electrical activity. A method includes obtaining a signal indicative of cardiac electrical activity, and using a first bandpass filter to produce a first filtered version thereof, using a second bandpass filter to produce a second filtered version thereof, wherein the first bandpass filter passes frequencies within a first frequency range, and the second bandpass filter passes frequencies within a second frequency range that is wider than the first frequency range. The method also includes selectively changing from using the first filtered version of the signal to monitor for a VS event, to using the second filtered version of the signal to monitor for a VS event, based on first criteria, and vice versa, based on second criteria.

11 Claims, 6 Drawing Sheets

(51) Int. Cl.
  *A61B 5/335* (2021.01)
  *A61B 5/352* (2021.01)
  *A61B 5/355* (2021.01)
  *A61B 5/361* (2021.01)
  *A61B 5/363* (2021.01)

(52) U.S. Cl.
  CPC .............. *A61B 5/355* (2021.01); *A61B 5/361* (2021.01); *A61B 5/363* (2021.01)

(58) Field of Classification Search
  CPC ......... A61B 5/363; A61B 5/316; A61B 5/686; A61B 5/7221
  See application file for complete search history.

(56) References Cited

U.S. PATENT DOCUMENTS

| | | | |
|---|---|---|---|
| 9,597,525 | B2 | 3/2017 | Cao et al. |
| 10,149,627 | B2* | 12/2018 | Allavatam ........... A61N 1/3956 |
| 10,328,274 | B2 | 6/2019 | Zhang et al. |
| 10,888,238 | B2 | 1/2021 | Allavatam et al. |
| 2003/0204215 | A1 | 10/2003 | Gunderson et al. |
| 2004/0199082 | A1 | 10/2004 | Ostroff et al. |
| 2007/0032829 | A1 | 2/2007 | Ostroff |
| 2008/0103535 | A1 | 5/2008 | Ostroff et al. |
| 2009/0018595 | A1* | 1/2009 | Bharmi ................ A61N 1/3925 607/14 |
| 2010/0280567 | A1 | 11/2010 | Gunderson |
| 2016/0325106 | A1 | 11/2016 | Cao et al. |
| 2017/0050037 | A1 | 2/2017 | Hahn et al. |
| 2017/0156617 | A1 | 6/2017 | Allavatam et al. |
| 2018/0064360 | A1* | 3/2018 | Siejko ................... A61B 5/364 |
| 2018/0318588 | A1 | 11/2018 | Dennis |
| 2019/0329038 | A1 | 10/2019 | Rhude |
| 2019/0350481 | A1* | 11/2019 | Sarkar ................... A61B 5/287 |
| 2019/0365267 | A1* | 12/2019 | Aranda Hernandez ...................... A61N 1/36507 |
| 2021/0282717 | A1 | 9/2021 | Loring et al. |

OTHER PUBLICATIONS

International Search Report & The Written Opinion of the International Searching Authority dated Oct. 12, 2022, International Application No. PCT/US2022/038392.

Boston Scientific, "The Impact of Smart Pass on Reducing Inappropriate Shocks for S-ICD," Boston Scientific Corporation, CRM-712201-AB, May 2020, 2 pages.

Boston Scientific, "The Evolution of S-ICD Technology," downloaded on Oct. 5, 2023, [—https://www.bostonscientific.com/en-US/products/defibrillators/emblem-s-icd-system/device-overview/specifications.html#:~:text=8.7%20years.1-,SMART%20Pass,-The%20SMART%20Pass], 3 pages.

Boston Scientific, "User's Manual—Subcutaneous Implantable Cardioverter Defibrillator," Boston Scientific Corporation, Jan. 2017, 72 pages.

International Preliminary Report on Patentability dated May 2, 2024, International Application No. PCT/US2022/038392.

Communication pursuant to Rules 161(1) and 162 EPC dated May 28, 2024, European Patent Application No. 22754692.6-1113.

Response to Communication pursuant to Rules 161(1) and 162 EPC dated Jul. 10, 2024, European Patent Application No. 22754692.6-1113.

* cited by examiner

IMPLANTABLE MEDICAL DEVICES, SYSTEMS AND METHODS FOR REDUCING T-WAVE OVERSENSING AND ARRHYTHMIA UNDERSENSING

PRIORITY CLAIM

This application claims priority to U.S. Provisional Patent Application No. 63/262,778, filed Oct. 20, 2021, which is incorporated herein by reference in its entirety.

FIELD

Embodiments described herein relate to implantable medical devices, systems, and methods for reducing T-wave oversensing and arrhythmia undersensing that may occur due to inappropriate filtering of a sensed signal indicative of cardiac electrical activity, such as, but not limited to, a far-field electrocardiogram (EGM).

A subcutaneous implantable cardioverter defibrillator (S-ICD) is a type of non-vascular ICD (NV-ICD) that monitors a patient's cardiac rhythm. When the S-ICD, or other type of NV-ICD, detects an episode of ventricular fibrillation (VF), which is a very fast, abnormal heart rhythm, the ICD delivers defibrillation energy to the heart muscle to cause the heart to return to its normal sinus rhythm (NSR). An NV-ICD, such as an S-ICD, is different from a traditional vascular ICD because the leads that run from the device housing to the heart are implanted extravascularly, e.g., under the patient's skin, instead of through the patient's veins and into the cardiac chambers. Beneficially, this allows the leads to be more easily implanted, removed and replaced.

NV-ICDs, such as, but not limited to, S-ICDs, are types of implantable medical devices (IMDs) that rely on accurate and reliable R-wave detections from a sensed signal indicative of cardiac electrical activity, such as an electrogram (EGM) or an electrocardiogram (ECG). This is especially true in an NV-ICD device that relies on sensing of a far-field EGM that is complex in morphology, incorporates the activity of a broader area of cardiac tissue, and can exhibit unique morphologies during different types of cardiac rhythms. NV-ICDs typically filter a sensed signal indicative of cardiac electrical activity in order to remove signal components that are not of interest, such as noise. However, inappropriate filtering of a sensed signal indicative of cardiac electrical activity could potentially lead to T-wave oversensing and/or arrhythmia undersensing.

SUMMARY

Certain embodiments of the present the present technology are directed to an apparatus comprising two or more electrodes, a sensing circuit, a first bandpass filter, a second bandpass filter, an R-wave detector, and a controller. The sensing circuit is coupleable to at least two of the electrodes to thereby sense a signal indicative of cardiac electrical activity. The first bandpass filter is configured to pass frequencies within a first frequency range and can be used to produce a first filtered version of the signal indicative of cardiac electrical activity. The second bandpass filter is configured to pass frequencies within a second frequency range and can be used to produce a second filtered version of the signal indicative of cardiac electrical activity, wherein the second frequency range is wider than the first frequency range. The controller is configured to cause one of the first or second filtered versions of the signal indicative of cardiac electrical activity to be provided to the R-wave detector. The R-wave detector is configured to monitor for a potential ventricular sensed (VS) event based on the one of the first or second filtered versions of the signal indicative of cardiac electrical activity, which is caused to be provided to the R-wave detector by the controller. The controller is also configured to selectively change from causing the first filtered version of the signal indicative of cardiac electrical activity to be provided to the R-wave detector, to causing the second filtered version of the signal indicative of cardiac electrical activity to be provided to the R-wave detector, and vice versa.

In accordance with certain embodiments, the first frequency range passed by the first bandpass filter is one of 6-25 Hz or 8-25 Hz, and the second frequency range passed by the second bandpass filter is 3-25 Hz. These are examples of embodiments where the second frequency range is wider than and encompasses the first frequency range. Other variations are also possible and within the scope of the embodiments described herein.

In accordance with certain embodiments, the controller is configured to determine whether one or more first criteria are satisfied, in response to a potential VS event being detected by the R-wave detector based on the first filtered version of the signal indicative of cardiac electrical activity. The controller is also configured to selectively change from causing the first filtered version of the signal indicative of cardiac electrical activity to be provided to the R-wave detector, to causing the second filtered version of the signal indicative of cardiac electrical activity to be provided to the R-wave detector, based on results of the determination of whether one or more first criteria are satisfied.

In accordance with certain embodiments, the controller is configured to determine whether one or more second criteria are satisfied, in response to a potential VS event being detected by the R-wave detector based on the second filtered version of the signal indicative of cardiac electrical activity. The controller is also configured to selectively change from causing the second filtered version of the signal indicative of cardiac electrical activity to be provided to the R-wave detector, to causing the first filtered version of the signal indicative of cardiac electrical activity to be provided to the R-wave detector, based on results of the determination of whether the one or more second criteria are satisfied. In accordance with certain embodiments, the one or more first criteria are configured to detect R-wave undersensing and/or reduce a chance of R-wave undersensing during an episode of ventricular tachycardiac (VT) or VF. In accordance with certain embodiments, the one or more second criteria are used by the controller to reduce a chance of T-wave oversensing causing a false detection of VT or VF.

In accordance with certain embodiments, the one or more first criteria include: (i) a prevalence of T-wave oversensing is below a first specified prevalence threshold, and a specified amount of most recently detected potential VS events each have a peak amplitude below a first specified amplitude threshold; (ii) a duration of time between the detected potential VS event and an immediately preceding detected potential VS event exceeds a first specified duration threshold; and (iii) a duration of time between the detected potential VS event and an immediately preceding detected potential VS event exceeds a second specified duration threshold, which is less than the first specified duration threshold, and a peak amplitude of the detected potential VS event is below a second specified amplitude threshold. In certain such embodiments, the controller changes from causing the first filtered version of the signal indicative of cardiac electrical activity to be provided to the R-wave detector, to causing the second filtered version of the signal indicative of cardiac electrical activity to be provided to the R-wave detector, in response to the controller determining that at least one of the criteria (i), (ii), or (iii) is true.

In accordance with certain embodiments, the one or more first criteria include: (iv) at least one of VT or VF is currently being detected. In certain such embodiments, the controller changes from causing the first filtered version of the signal indicative of cardiac electrical activity to be provided to the R-wave detector, to causing the second filtered version of the signal indicative of cardiac electrical activity to be provided to the R-wave detector, in response to the controller determining that the criterion (iv) is true.

In accordance with certain embodiments, the one or more second criteria include: (v) neither VT nor VF is currently being detected; and (vi) a specified amount of most recently detected potential VS events each have a peak amplitude above a specified amplitude threshold, or have been classified as having been detected due to T-wave oversensing. In certain such embodiments, the controller changes from using the second filtered version of the signal indicative of cardiac electrical activity to monitor for a potential VS event, to using the first filtered version of the signal indicative of cardiac electrical activity to monitor for a potential VS event, in response to the controller determining that both criteria (v) and (vi) are true.

In accordance with certain embodiments, the first and second filtered versions of the signal indicative of cardiac electrical activity are produced in parallel by passing the signal indicative of cardiac electrical activity through the first filter included within a first channel, and also separately passing the signal indicative of cardiac electrical activity through the second filter included in a second channel. In certain such embodiments, the controller controls whether the first channel or the second channel is coupled to the R-wave detector.

In accordance with certain embodiments, the R-wave detector is configured to detect when the first filtered version of the signal indicative of cardiac electrical activity, or the second filtered version of the signal indicative of cardiac electrical activity, crosses a sensing threshold to thereby detect a threshold crossing indicative of a detected potential VS event.

In accordance with certain embodiments, the apparatus comprises an implantable medical device (IMD) and the signal indicative of cardiac electrical activity comprises one of a far-field EGM or a far-field ECG.

Certain embodiments of the present the present technology are directed a method for adjusting filtering of a signal indicative of cardiac electrical activity, based upon which monitoring for potential VS events occurs. In certain embodiments, the method comprises: (a) providing a first bandpass filter configured to pass frequencies within a first frequency range and that can be used to produce a first filtered version of the signal indicative of cardiac electrical activity, and a second bandpass filter configured to pass frequencies within a second frequency range and that can be used to produce a second filtered version of the signal indicative of cardiac electrical activity, wherein the second frequency range is wider than the first frequency range; and (b) selectively changing from using the first filtered version of the signal indicative of cardiac electrical activity to monitor for a VS event, to using the second filtered version of the signal indicative of cardiac electrical activity to monitor for a VS event, and vice versa.

In accordance with certain embodiments, the first frequency range passed by the first bandpass filter is one of 6-25 Hz or 8-25 Hz, and the second frequency range passed by the second bandpass filter is 3-25 Hz. These are examples of embodiments where the second frequency range is wider than and encompasses the first frequency range.

In accordance with certain embodiments, the (b) selectively changing comprises: (b.1) using the first filtered version of the signal indicative of cardiac electrical activity to monitor for a potential VS event, and in response to a potential VS event being detected using the first filtered version of the signal indicative of cardiac electrical activity, determining whether one or more first criteria are satisfied; and (b.2) based on results of the determining whether one or more first criterion are satisfied, changing from using the first filtered version of the signal indicative of cardiac electrical activity to monitor for a potential VS event, to using the second filtered version of the signal indicative of cardiac electrical activity to monitor for a potential VS event.

In accordance with certain embodiments, the (b) selectively changing also comprises: (b.3) in response to a potential VS event being detected using the second filtered version of the signal indicative of cardiac electrical activity, determining whether one or more second criteria are satisfied; and (b.4) based on results of the determining whether one or more second criteria are satisfied, changing from using the second filtered version of the signal indicative of cardiac electrical activity to monitor for a potential VS event, to using the first filtered version of the signal indicative of cardiac electrical activity to monitor for a potential VS event.

In accordance with certain embodiments, the one or more first criteria are configured to at least one of: detect R-wave undersensing; and reduce a chance of R-wave undersensing during an episode of at least one of VT or VF. In accordance with certain embodiments, the one or more second criteria are used to reduce a chance of T-wave oversensing causing a false detection of VT or VF.

In accordance with certain embodiments, the one or more first criteria include: (i) a prevalence of T-wave oversensing is below a first specified prevalence threshold, and a specified amount of most recently detected potential VS events each have a peak amplitude below a first specified amplitude threshold; (ii) a duration of time between the detected potential VS event and an immediately preceding detected potential VS event exceeds a first specified duration threshold; and (iii) a duration of time between the detected potential VS event and an immediately preceding detected potential VS event exceeds a second specified duration threshold, which is less than the first specified duration threshold, and a peak amplitude of the detected potential VS event is below a specified amplitude threshold; and wherein the (b) changing from using the first filtered version of the signal indicative of cardiac electrical activity to monitor for a VS event, to using the second filtered version of the signal indicative of cardiac electrical activity to monitor for a VS event, occurs in response to determining that at least one of the criteria (i), (ii), or (iii) is true.

In accordance with certain embodiments, the one or more first criteria includes: (iv) at least one of VT or VF is currently being detected; and the (b) changing from using the first filtered version of the signal indicative of cardiac electrical activity to monitor for a VS event, to using the second filtered version of the signal indicative of cardiac electrical activity to monitor for a VS event, occurs in response to determining that the criterion (iv) is true.

In accordance with certain embodiments, the one or more second criteria include: (v) neither VT nor VF is currently being detected; and (vi) a specified amount of most recently detected potential VS events each have a peak amplitude above a specified amplitude threshold, or have been classified as having been detected due to T-wave oversensing; wherein the changing from using the second filtered version of the signal indicative of cardiac electrical activity to monitor for a potential VS event, to using the first filtered version of the signal indicative of cardiac electrical activity to monitor for a potential VS event, occurs in response to determining that both criteria (v) and (vi) are true.

In accordance with certain embodiments, the first and second filtered versions of the signal indicative of cardiac electrical activity are produced in parallel by passing the signal indicative of cardiac electrical activity through the first filter included within a first channel, and also separately passing the signal indicative of cardiac electrical activity through the second filter included in a second channel. In such an embodiment, the (b) selectively changing comprises controlling whether the first channel or the second channel is coupled to the R-wave detector.

In accordance with certain embodiments, the method further comprises monitoring for a VS event by detecting when the first filtered version of the signal indicative of cardiac electrical activity, or the second filtered version of the signal indicative of cardiac electrical activity, crosses a sensing threshold to thereby detect a threshold crossing indicative of a detected potential VS event.

In accordance with certain embodiments, the method is performed by an IMD and the signal indicative of cardiac electrical activity comprises one of a far-field EGM signal or a far-field ECG.

A method according to an embodiment of the present technology comprises obtaining a signal indicative of cardiac electrical activity, and using a first bandpass filter to filter the signal indicative of cardiac electrical activity to thereby produce a first filtered version of the signal indicative of cardiac electrical activity, wherein the first bandpass filter is configured to pass frequencies within a first frequency range. The method also comprises using a second bandpass filter to filter the signal indicative of cardiac electrical activity to thereby produce a second filtered version of the signal indicative of cardiac electrical activity, wherein the second bandpass filter is configured to pass frequencies within a second frequency range that is wider than the first frequency range and encompasses the first frequency range. The method also includes selectively changing from using the first filtered version of the signal indicative of cardiac electrical activity to monitor for a VS event, to using the second filtered version of the signal indicative of cardiac electrical activity to monitor for a VS event, based on first criteria. The method further includes selectively changing from using the second filtered version of the signal indicative of cardiac electrical activity to monitor for a VS event, to using the first filtered version of the signal indicative of cardiac electrical activity to monitor for a VS event, based on second criteria.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

As explained above, many types of IMDs, such as NV-ICDs, rely on accurate and reliable R-wave detection from a sensed EGM or ECG. This is especially true in an NV-ICD, which relies on sensing of a far-field cardiac signal, and more specifically a far-field EGM that is complex in morphology and can exhibits unique morphologies during different rhythms.

In an NV-ICD, a sensed EGM is more similar to a surface ECG than an intracardiac EGM (IEGM) in terms of frequency content and signal morphology, since the sensing electrodes are located outside of the heart. Through experimentation it has been determined that in the frequency domain, R-waves during normal sinus rhythm (NSR) have most of their power within the range of 1-25 Hz; whereas T-waves during NSR have most of their power within the range of 1-10 Hz; and R-waves during an episode of ventricular fibrillation (VF) or ventricular tachycardiac (VT) have most of their power spread over the range of 1-15 Hz. Due to the overlap in the frequency domain of T-waves during NSR and R-waves during an episode of VF or VT, it is likely that a filter that attenuates T-waves during NSR would also attenuate R-waves during an episode of VF or VT. Accordingly, if an IMD filters a far-field EGM using a single filter having a bandpass frequency (BPF) of 1-10 Hz, such a filter may inadvertently attenuate R-waves during an episode of VF or VT, resulting in R-wave undersensing that may lead to VF or VT undersensing, which is undesirable and can lead to therapy delivery being inappropriately withheld. On the other hand, if an IMD filters a far-field EGM using a single filter having a BPF of 1-25 Hz in order to maintain R-wave amplitudes during episodes of VF or VT, such a filter cannot effectively attenuate T-waves, which may result in T-wave oversensing (TWO) that may lead to inappropriate oversensing of VT and/or VF, which is undesirable and can lead to inappropriate VT and/or VF therapy delivery.

Certain embodiments of the present technology described herein have been developed to deal with the conflicting demands for a filter during different cardiac rhythms. More specifically, in accordance with certain embodiments of the present technology, which are described in more detail below, multiple different filters are simultaneously used to filter an EGM (or ECG) on multiple channels, and automatic switching between the channels (or more specifically, between the use of different filtered signals) is performed for R-wave sensing to reduce (and preferably minimize) both T-wave oversensing and R-wave undersensing, which should also reduce (and preferably minimize) VF and VT oversensing, as well as VF and VT undersensing.

Figure 1:
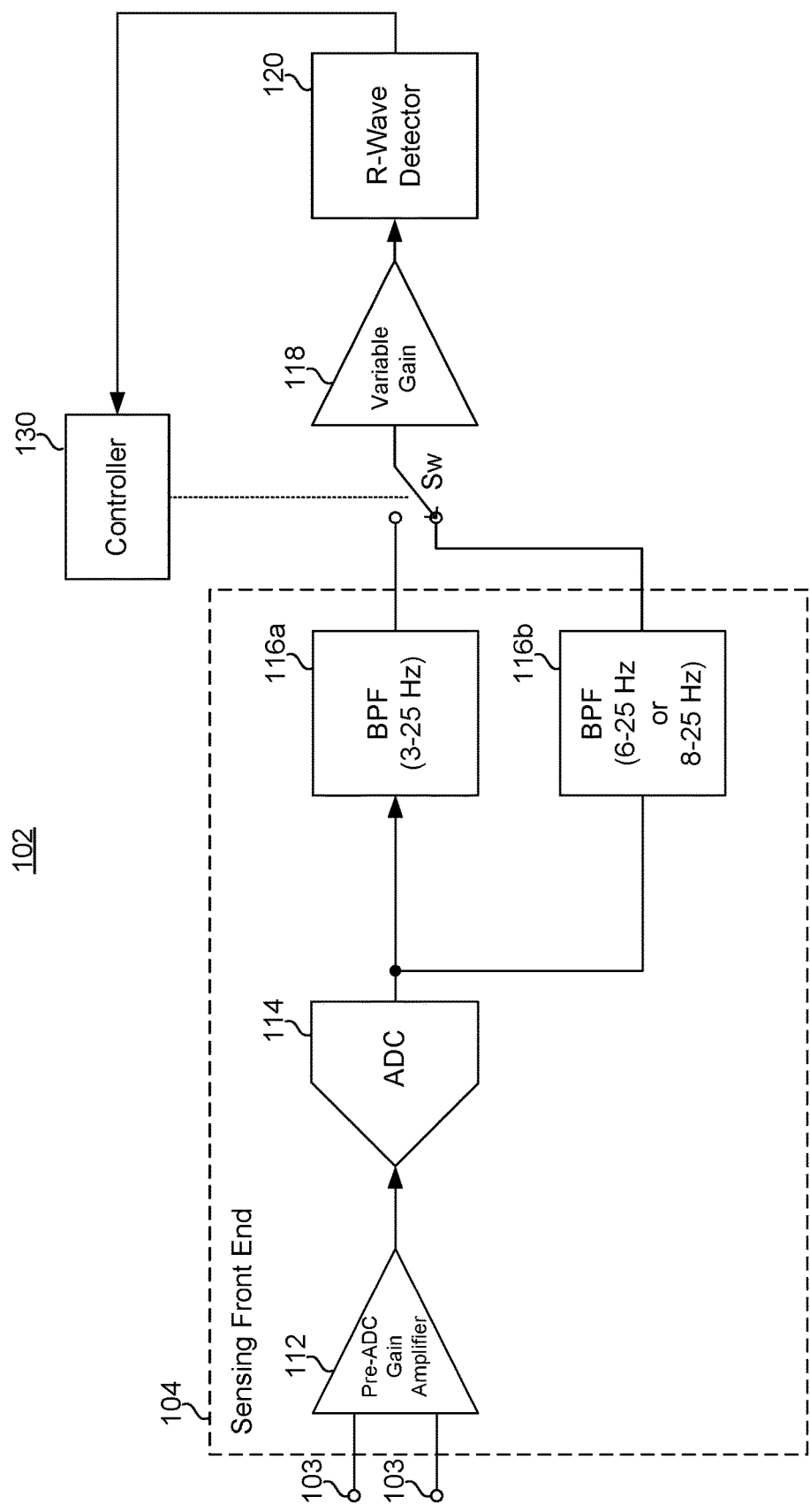
FIG. 1 is a high level block diagram of sensing and R-wave detection circuitry of an IMD, according to the embodiment of the present technology.

FIG. 1 is a high level block diagram of sensing and R-wave detection circuitry 102 of an IMD, according to the embodiment of the present technology. The elements of the circuitry 102 shown in the dashed block labels 104 are components of a sensing front end 104 of an IMD, which can also be referred to as a sampling front end 104, or more succinctly as a front end 104. Referring to FIG. 1, the circuitry 102 is shown as including an analog amplifier 112, an analog-to-digital converter (ADC) 114, filters 116a and 116b, a switch Sw, a digital amplifier 118, an R-wave detector 120, and a controller 130. The analog amplifier 112, which can be a fixed gain pre-ADC amplifier, preferably provides enough gain to the sensed EGM (or ECG) that is to be converted by the ADC 114, so that the ADC 114 can operate properly, wherein the ADC 114 can be a high resolution (e.g., 14-bit) ADC, but is not limited thereto. For example, if a sensed EGM is in the millivolt (mV) range, and the ADC 114 has a reference voltage of 1 volt (V), then the analog amplifier 112 may provide a gain of about 1000 V/V, to enable the ADC 114 to operate properly. For the purpose of this discussion, the signal that is provided to the amplifier 112, and amplified by the amplifier 112, is often referred to as an ECG/EGM signal, or more generally as a signal indicative of cardiac electrical activity. Such a signal indicative of cardiac electrical activity is sensed by the amplifier using electrodes 103, which can be directly coupled to the amplifier 112, or can be coupled by a via switching circuitry to the amplifier 112. The amplifier 112 is one example of a sensing circuit coupleable to at least two of the electrodes 103 to thereby sense a signal indicative of cardiac electrical activity.

The amplified analog signal, which is output by the analog amplifier 112, is converted to a digital signal by the ADC 114. The digital signal is separately filtered, in parallel, by the filters 116a and 116b. The switch Sw (that is controlled by the controller 130) controls whether the signal output by the filter 116a, or the signal output by the filter 116b, is provided to the amplifier 118 and then to the R-wave detector 120. In accordance with certain embodiments, the filter 116a is a bandpass filter (BPF) having a bandpass frequency of 3-25 Hz, and the filter 116b is a BPF having a bandpass frequency of 6-25 Hz. Alternatively, the filter 116b can have a bandpass frequency of 8-25 Hz. Other variations are also possible and within the scope of the present technology. For example, the filter 116a can have a bandpass frequency of 0-25 Hz, and the filter 116b can have a bandpass frequency of 7-24 Hz or 9-24 Hz. The filters 116a and 116b can also be referred to herein more generally as a conservative filter 116a and an aggressive filter 116b. In other words, the filter 116b having the narrower passband is considered to be more aggressive than the filter 116a having the wider passband.

The R-wave detector 120 can perform R-wave detection in any one of various different manners. For example, the R-wave detector 120 can compare the signal output by the amplifier 118 to a dynamic sensing threshold, wherein the signal output by the amplifier 118 is a filtered and amplified version of the sensed ECG/EGM signal. More specifically, the R-wave detector 120 can detect an R-wave whenever the filtered and amplified version of the sensed ECG/EGM signal crosses the dynamic sensing threshold. Each such threshold crossing can start a sense refractory period, during which the filtered and amplified version of the sensed ECG/EGM signal is not compared to the dynamic sensing threshold, and during which a peak of the filtered and amplified version of the sensed ECG/EGM signal within the sense refractory period is identified, wherein the peak is the peak R-wave amplitude. At the end of the sense refractory period, the dynamic sensing threshold can be set to a programmed percentage (e.g., 62.5%) of the peak R-wave amplitude. For an example, if the peak R-wave amplitude is 7 millivolts (mV), then the dynamic sensing threshold can be set to 3.75 mV at the end of the sense refractory period. The dynamic sensing threshold can then remain at that amplitude (i.e., at 3.75 mV in this example) for a programmed decay delay (e.g., 60 milliseconds (msec)) before beginning to decay at a programmed decay rate (e.g., 1 mV per second) until reaching a maximum sensitivity level, which may or may not be the same as a minimum magnitude of the dynamic sensing threshold. Other variations are also possible and within the scope of the present technology. For another example, it is possible that the filtered and amplified version of the sensed ECG/EGM signal his compared to a non-dynamic (aka fixed) sensing threshold, instead of a dynamic sensing threshold.

Figure 2:
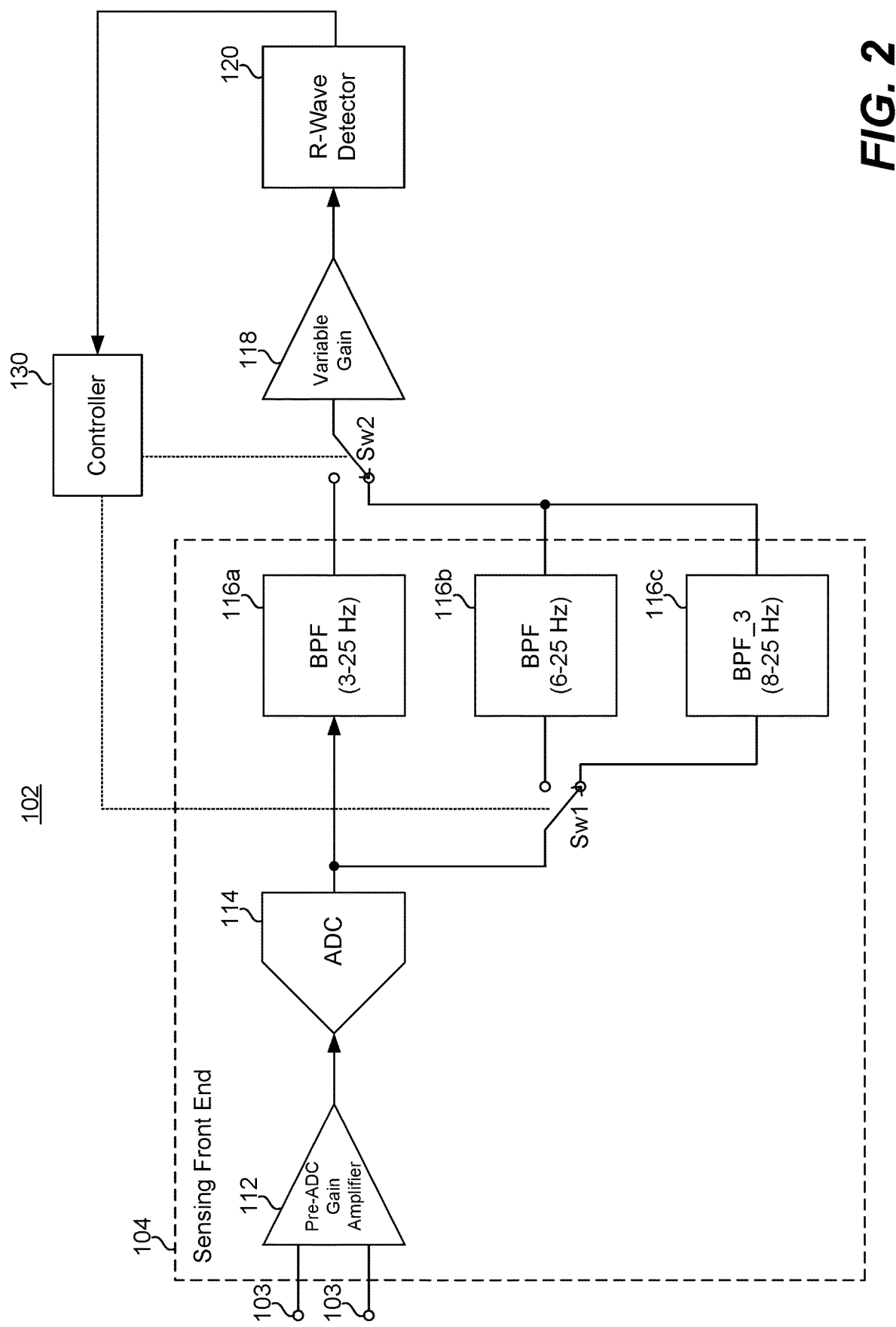
FIG. 2 is a high level block diagram of sensing and R-wave detection circuitry, according to another embodiment of the present technology.

FIG. 2 is a high level block diagram of the sensing and R-wave detection circuitry 102, according to another embodiment of the present technology. Elements in FIG. 2 that are the same as or similar to elements FIG. 1 are labeled the same and need not be described again. In the embodiment of FIG. 2 there is an additional filter 116c and an additional switch Sw1 that provides the amplified (and digitized) version of the sensed ECG/EGM signal to either the filter 116b or the filter 116c as controlled by the controller 130, such that the amplified version of the sensed ECG/EGM signal is filtered in parallel by the filter 116a and one of the filters 116b or 116c. In FIG. 2, a switch Sw2 is controlled to pass either the output of the filter 116a, or the output of a selected one of the filters 116b or 116c to the amplifier 118 and R-wave detector 120. In the embodiment of FIG. 2, a clinician can utilize a user interface (e.g., a graphical user interface (GUI)) to select one of the filters 116b or 116c based on characteristics of a patient's sensed ECG/EGM signal, such as, but not limited to, low amplitude T-waves, high amplitude T-waves, or low amplitude R-waves. The controller 130 autonomously selects between the filter 116a and the one of the filters 116b or 116c (that was selected by the clinician) based on various different criteria, as described in additional detail below. The various filters 116a, 116b, and 116c can be referred to collectively as filters 116, or individually as a filter 116.

In the embodiments shown in FIGS. 1 and 2, different filters 116 are designed to either aggressively attenuate T-wave amplitudes, to varying degrees, or to preserve R-wave amplitudes. Among the filters 116, the filter 116c that has a bandpass frequency of 8-25 Hz provides the greatest degree of T-wave attenuation, while the filter 116a that has a bandpass frequency of 3-25 Hz maintains the highest R-wave amplitudes during episodes of VF or VT. Compared with the filter 116c having the bandpass frequency of 8-25 Hz, the filter 116b having the bandpass frequency of 6-25 Hz provides less T-wave attenuation but preserves greater R-wave amplitudes during episodes of VF or VT, and thus, is suitable for patients with small T-waves. Explained another way, the filter 116c having the narrowest bandpass frequency range is the most aggressive filter; the filter 116b having the second narrowest bandpass frequency range is the second most aggressive filter; and the filter 116a having the widest bandpass frequency range is the least aggressive filter.

In the embodiments shown in FIGS. 1 and 2, the signal output by the amplifier 112 can be more generally referred to as a signal indicative of cardiac electrical activity. Similarly, the signal output by the ADC 114 can also be referred to generally as a signal indicative of cardiac electrical activity, or can be referred to more specifically as a digitized version of a signal indicative of cardiac electrical activity. In the embodiments shown in FIGS. 1 and 2, since the ADC 114 converts the signal indicative of cardiac electrical activity to a digital signal, the filters 116 perform their filtering in the digital domain, and thus, can be referred to as digital filters. In alternative embodiments of the present technology, the ADC 114 can be eliminated, and the filters 116 can be analog filters that perform their filtering in the analog domain. In still another embodiment, the ADC is upstream of the filters 116, rather than being downstream of the filters 116 (as was the case in FIGS. 1 and 2).

In accordance with certain embodiments of the present technology, the R-wave detector 120 is configured to monitor for R waves, which are ventricular sensed (VS) events. Accordingly, it can also be said that the R-wave detector 120 is configured to monitor for VS events. Whenever the R-wave detector 120 detects a VS event, the detected event can be referred to as a potential VS event, since it is possible that the detection is a false positive. In the embodiment of FIG. 1, the less aggressive filter 116a produces a filtered version of the signal indicative of cardiac electrical activity, and the more aggressive filter 116b produces another filtered version of the signal indicative of cardiac electrical activity. In specific embodiments, the less aggressive filter 116a is configured to pass frequencies within a specified frequency range (e.g., 3-25 Hz), and the more aggressive filter 116b is configured to pass frequencies within another specified frequency range (e.g., 6-25 Hz or 8-25 Hz) that is narrower than the first frequency range.

Still referring to the embodiment of FIG. 1, in accordance with certain embodiments, the controller 130 initially controls the switch Sw to select the output of the more aggressive filter 116b, and thus, the R-wave detector 120 initially monitors for a potential VS event using the more aggressively filtered version of the signal indicative of cardiac electrical activity. In certain such embodiments, in response to a potential VS event being detected using the more aggressively filtered version of the signal indicative of cardiac electrical activity, the controller 130 determines whether certain first criteria are satisfied, so that the controller 130 can determine whether it would be better to utilize the less aggressively filtered version of the signal indicative of cardiac electrical activity to monitor for VS events. In other words, in order to determine whether it would be better to utilize the less aggressively filtered version of the signal indicative of cardiac electrical activity to monitor for VS events, the controller 130 determines whether one or more first criteria are satisfied, in response to a potential VS event being detected by the R-wave detector 120 based on the first filtered version of the signal indicative of cardiac electrical activity. The first criteria are used to determine whether use of the more aggressive filter 116b is likely causing R-wave undersensing, and also reduces the chance of R-wave undersensing during an episode of VT or VF.

In accordance with certain embodiments, the controller 130 determines whether use of the more aggressive filter (116b or 116c) is likely causing R-wave undersensing, by determining whether a prevalence of T-wave oversensing (TWO) is below a specified prevalence threshold, and whether a specified amount of most recently detected potential VS events each have a peak amplitude below a second specified amplitude threshold. If both of those criteria are true, then the controller 130 determines that the use of the more aggressive filter (116b or 116c) is likely causing R-wave undersensing, and the controller 130 can control one or more switches to cause the less aggressively filtered version of the signal indicative of cardiac electrical activity (output by the filter 116a) to be provided to the R-wave detector 120 to monitor for VS events. For an example, if T-wave oversensing was not detected in at least N out of the M of the most recently detected potential VS events (e.g., four out of the seven most recently detected potential VS events, but not limited thereto), or was not detected in at least a certain percentage of the most recently detected potential VS events (e.g., 60% of the ten most recently detected potential VS events, but not limited thereto), then the controller 130 can determine that the prevalence of T-wave oversensing (TWO) is below the specified prevalence threshold. If peak amplitudes associated with each of the X most recent detected potential VS events (e.g., the three most recent detected potential VS events, but not limited thereto) are below a second specified amplitude threshold (e.g., set at two times a maximum R-wave sensitivity threshold, but not limited thereto), then the controller 130 can determine that the specified amount of most recently detected potential VS events each have a peak amplitude below the second specified amplitude threshold. The second specified amplitude threshold, can be the same as, or different than, the first specified amplitude threshold referred to above.

Additionally, or alternatively, the controller 130 can determine whether use of the more aggressive filter (116b or 116c) is likely causing R-wave undersensing by determining whether a duration of time between the detected potential VS event and an immediately preceding detected potential VS event exceeds a first specified duration threshold (e.g., 3 seconds, but not limited thereto). If this criterion is true, then the controller 130 determines that the use of the more aggressive filter (116b or 116c) is likely causing R-wave undersensing, and the controller 130 can control one or more switches to cause the less aggressively filtered version of the signal indicative of cardiac electrical activity (output by the less aggressive filter 116a) to be provided to the R-wave detector 120 to monitor for VS events.

Additionally, or alternatively, the controller 130 can determine whether use of the more aggressive filter (116b or 116c) is likely causing R-wave undersensing by determining whether a duration of time between the detected potential VS event and an immediately preceding detected potential VS event exceeds a second specified duration threshold (e.g., 1.5 seconds, but not limited thereto), which is less than the first specified duration threshold (e.g., 3 seconds, but not limited thereto), and a peak amplitude of the detected potential VS event is below a third specified amplitude threshold (e.g., set at four times a maximum R-wave sensitivity threshold, but not limited thereto). If these criteria are true, then the controller 130 determines that the use of the more aggressive filter (116b or 116c) is likely causing R-wave undersensing, and the controller 130 can cause the less aggressively filtered version of the signal indicative of cardiac electrical activity (output by the filter 116a) to be provided to the R-wave detector 120 to monitor for VS events. Instead of just considering whether the immediately preceding detected potential VS event exceeds the second specified duration threshold (e.g., 1.5 seconds, but not limited thereto), there can instead be a determination of whether a certain amount (e.g., X out of Y, or a specified percentage) of a plurality of the preceding detected potential VS event exceeds the second specified duration threshold (e.g., 1.5 seconds, but not limited thereto). The third specified amplitude threshold, can be the same as, or different than, the first specified amplitude threshold referred to above, and can be the same as, or different than, the second specified amplitude threshold referred to above. Other variations are also possible, and within the scope of the embodiments described herein.

In accordance with certain embodiments, the controller 130 can also determine that it would be better to utilize the less aggressively filtered version of the signal indicative of cardiac electrical activity (output by the filter 116a), to monitor for VS events, if VT or VF is being detected. This is because it would be undesirable to terminate treatment for VT or VF in response to a false determination that the VT or VF episode ended, which false detection may be caused by R-wave undersensing.

Once the controller 130 determines that it would be better to utilize the less aggressively filtered version of the signal indicative of cardiac electrical activity, to monitor for VS events, the controller 130 controls one or more switches (e.g., the switch Sw in FIG. 1, or the switch Sw2 in FIG. 2) so that the less aggressively filtered version of the signal indicative of cardiac electrical activity (output by the filter 116a) is provided to the amplifier 118 and then to the R-wave detector 120. The R-wave detector 120 then monitors for a potential VS event using the less aggressively filtered version of the signal indicative of cardiac electrical activity. Thereafter, in response to the R-wave detector 120 detecting a potential VS event using the less aggressively filtered version of the signal indicative of cardiac electrical activity, the controller 130 determines whether certain second criteria are satisfied, so that the controller 130 can determine whether it would be better to go back to utilizing the more aggressively filtered version of the signal indicative of cardiac electrical activity to monitor for VS events. The second criteria are used by the controller 130 to reduce a chance of T-wave oversensing causing a false detection of VT or VF.

In accordance with certain embodiments, the second criteria, which are used by the controller 130 (to determine whether it would be better to go back to utilizing the more aggressively filtered version of the signal indicative of cardiac electrical activity to monitor for VS events) include whether neither VT nor VF is currently being detected, and a specified amount of most recently detected potential VS events each have a peak amplitude above a third specified amplitude threshold (e.g., set to four times a maximum R-wave sensitivity threshold, but not limited thereto) or have been classified as having been detected due to T-wave oversensing. For an example, if T-wave oversensing was detected in at least N out of the M of the most recently detected potential VS events (e.g., four out of the seven most recently detected potential VS events, but not limited thereto), or was detected in at least a certain percentage of the most recently detected potential VS events (e.g., 60% of the ten most recently detected potential VS events), then the controller 130 can determine that the prevalence of T-wave oversensing (TWO) is above a specified prevalence threshold. The controller 130 can then change from using the less aggressive filtered version of the signal indicative of cardiac electrical activity to monitor for a potential VS event, to using the more aggressive filtered version of the signal indicative of cardiac electrical activity to monitor for a potential VS event, in response to the controller 130 determining that these second criteria are true. The second criteria can alternative, or additionally, involve a determination of whether a specified amount of time (e.g., 60 seconds) has elapsed since there was a switch from the more aggressive filter to the less aggressive filter. If the specified amount of time (e.g., 60 seconds) has elapsed since there was a switch from the more aggressive filter to the less aggressive filter, then the controller 130 can then change from using the less aggressive filtered version of the signal indicative of cardiac electrical activity to monitor for a potential VS event, to using the more aggressive filtered version of the signal indicative of cardiac electrical activity to monitor for a potential VS event. The third specified amplitude threshold, can be the same as, or different than, the first specified amplitude threshold referred to above, and can be the same as, or different than, the second specified amplitude threshold referred to above. Other variations are also possible and within the scope of the embodiments described herein.

Figure 3:
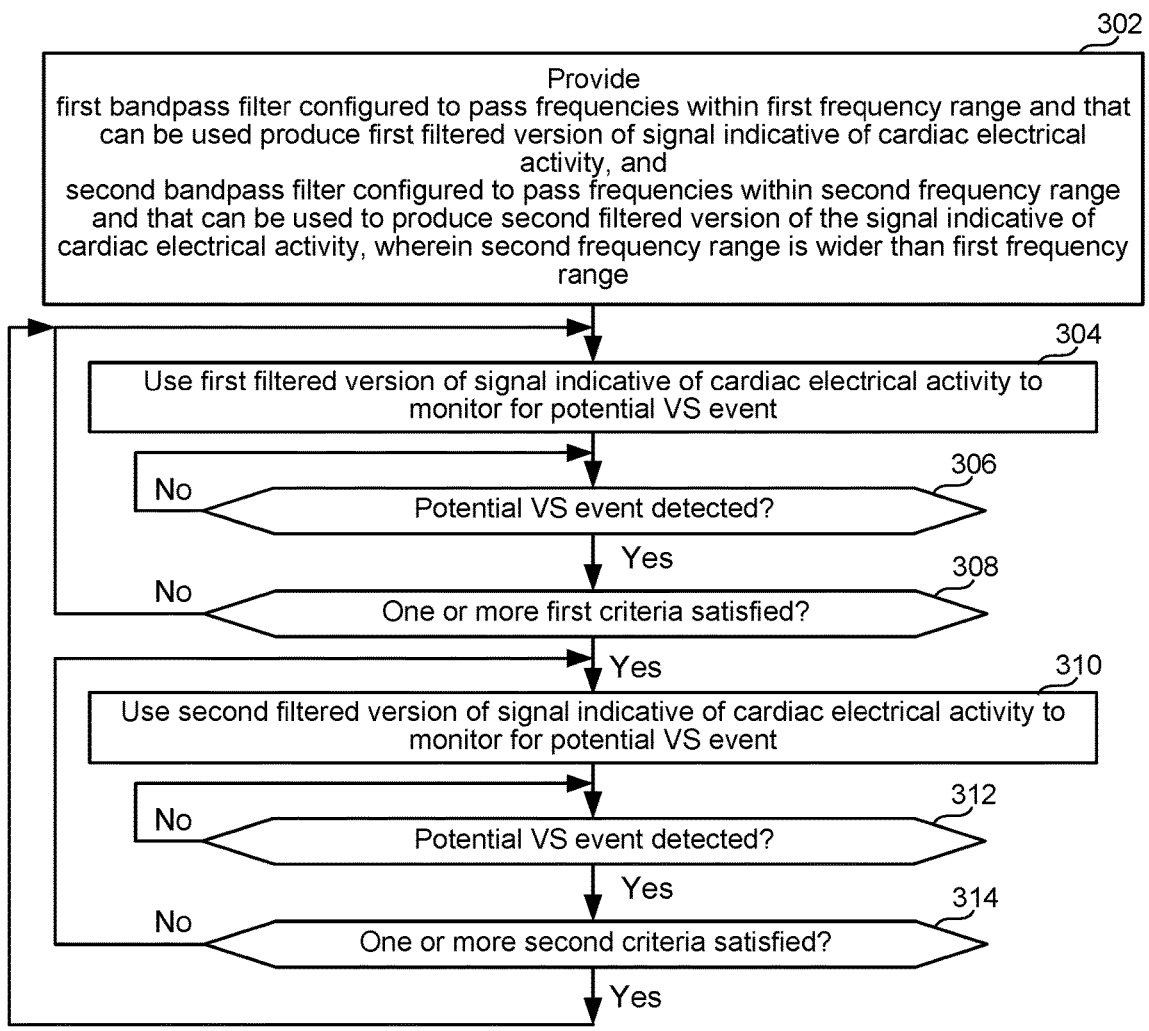
FIG. 3 is a high level flow diagram used to summarize methods, according to certain embodiments of the present technology, for adjusting filtering of a signal indicative of cardiac electrical activity, based upon which monitoring for potential VS events occurs.

The high level flow diagram of FIG. 3 will now be used to summarize methods, according to certain embodiments of the present technology, for adjusting filtering of a signal indicative of cardiac electrical activity, based upon which monitoring for potential VS events occurs. Referring to FIG. 3, step 302 involves providing a first bandpass filter configured to pass frequencies within a first frequency range and that can be used produce a first filtered version of the signal indicative of cardiac electrical activity, and a second bandpass filter configured to pass frequencies within a second frequency range and that can be used to produce a second filtered version of the signal indicative of cardiac electrical activity, wherein the second frequency range is wider than the first frequency range. Accordingly, the first bandpass filter proves for more aggressive filtering than the second bandpass filter. For an example, the first bandpass filter can be the filter 116b or 116c, and the second bandpass filter can be the filter 116a, but are not limited thereto.

In accordance with certain embodiments, the first frequency range passed by the first bandpass filter is 3-25 Hz, and the second frequency range passed by the second bandpass filter is one of 6-25 Hz or 8-25 Hz. Other variations are also possible and within the scope of the present technology. For example, the first frequency range passed by the first bandpass filter can be 0-25 Hz, and the second frequency range passed by the second bandpass filter can be 7-24 Hz or 9-24 Hz.

Step 304 involves using the first (more aggressively) filtered version of the signal indicative of cardiac electrical activity to monitor for a potential VS event. At step 306 there is a determination of whether a VS event was detected. Step 306 can be performed, for example, by determining whether the first filtered version of the signal indicative of cardiac electrical activity crosses a dynamic (or fixed) sensing threshold to thereby detect a threshold crossing indicative of a detected potential VS event. If the answer to the determination at step 306 is No, then step 306 is repeated until the answer to the determination at step 306 is Yes, at which point flow goes to step 308. The answer to the determination at step 306 can be Yes, for example, when the first filtered version of the signal indicative of cardiac electrical activity crosses the dynamic (or fixed) sensing threshold.

At step 308, there is a determination of whether one or more first criteria are satisfied. In other words, in response to a potential VS event being detected using the first filtered version of the signal indicative of cardiac electrical activity, there is a determination of whether one or more first criteria are satisfied. If one or more first criteria are not satisfied, then flow returns to step 304 and the first filtered version of the signal indicative of cardiac electrical activity is used to monitor for a next potential VS event. If one or more first criteria are satisfied, then flow goes to step 310. The one or more first criteria can be used to detect R-wave undersensing, and to reduce a chance of R-wave undersensing during an episode of VT or VF.

Step 310 involves using the second (less aggressively) filtered version of the signal indicative of cardiac electrical activity to monitor for a potential VS event. Accordingly, it can be appreciated that based on the results of determining whether one or more first criterion are satisfied, there is a selective changing from using the first (more aggressively) filtered version of the signal indicative of cardiac electrical activity to monitor for a potential VS event, to using the second (less aggressively) filtered version of the signal indicative of cardiac electrical activity to monitor for a potential VS event.

At step 312 there is a determination of whether a VS event was detected. If the answer to the determination at step 312 is No, then step 310 is repeated until the answer to the determination at step 312 is Yes, at which point flow goes to step 314. Step 312 can be performed, for example, by determining whether the second filtered version of the signal indicative of cardiac electrical activity crosses a dynamic (or fixed) sensing threshold to thereby detect a threshold crossing indicative of a detected potential VS event. The answer to the determination at step 312 can be Yes, for example, when the second filtered version of the signal indicative of cardiac electrical activity crosses the dynamic (or fixed) sensing threshold.

At step 314, there is a determination of whether one or more second criteria are satisfied. In other words, in response to a potential VS event being detected using the second filtered version of the signal indicative of cardiac electrical activity, there is a determination of whether one or more second criteria are satisfied. If one or more second criteria are not satisfied, then flow returns to step 310 and the second filtered version of the signal indicative of cardiac electrical activity is used to monitor for the next potential VS event. If one or more second criteria are satisfied, then flow returns to step 304, and the first filtered version of the signal indicative of cardiac electrical activity is used to monitor for a potential VS event. The one or more second criteria can be used to reduce a chance of T-wave oversensing or causing a false detection of VT or VF.

In an alternative embodiment, steps 310, 312, and 314 occur prior to steps 304, 306, and 308.

Figure 4:
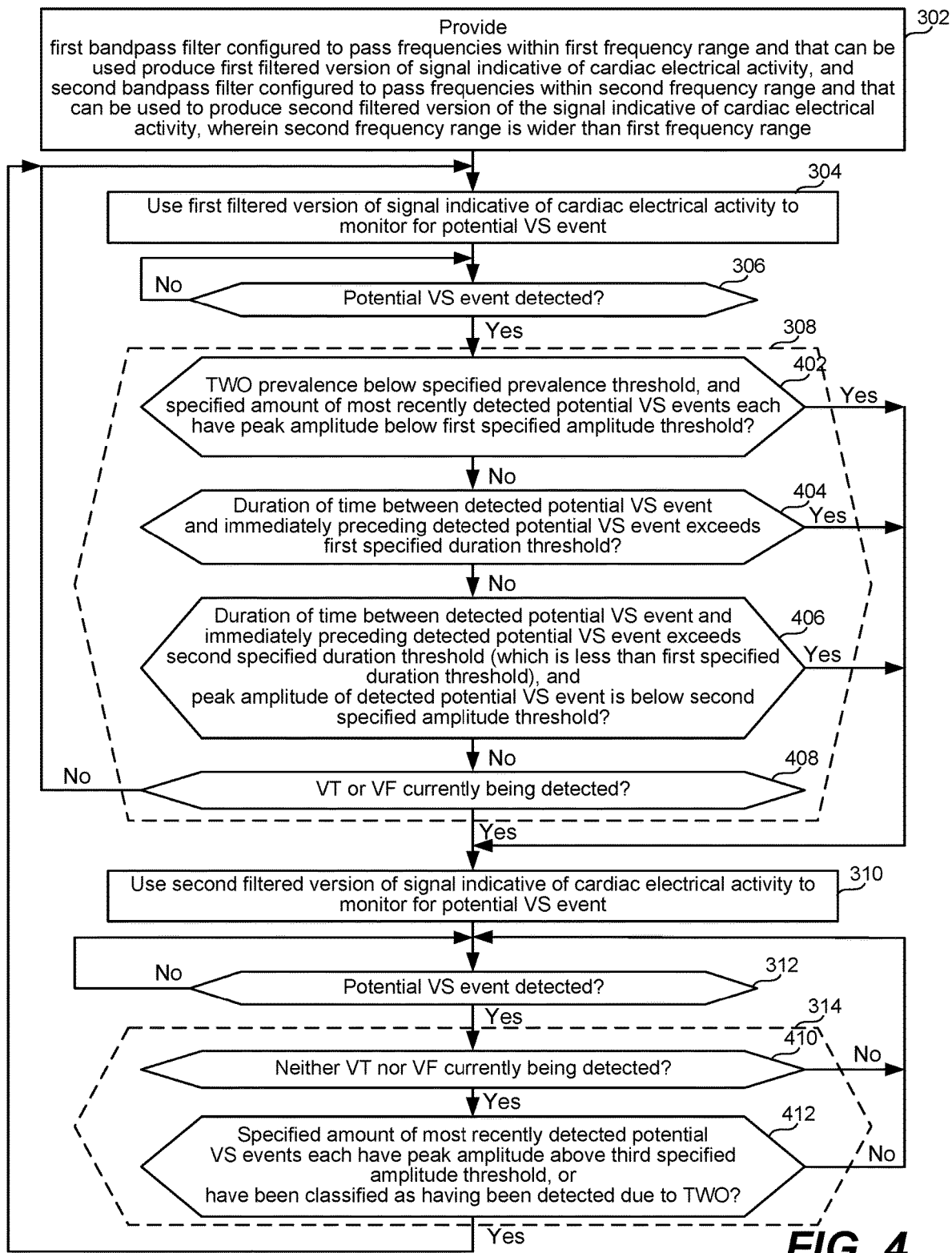
FIG. 4 is a high level flow diagram that is used to provide additional details of some of the steps introduced in FIG. 3, according to certain embodiments of the present technology.

The flow diagram of FIG. 4 will now be used to explain additional details of the first and second criteria referred to in steps 308 and 314, according to certain embodiments of the present technology. Steps in FIG. 4 that are the labeled the same as in FIG. 3 need not be described again.

In FIG. 4, step 308 is shows as being broken down into steps 402, 404, 406, and 408, which are used to determine whether various first criteria are true. At step 402 there is a determination of whether a prevalence of T-wave oversensing (TWO) is below a specified prevalence threshold, and a specified amount of most recently detected potential VS events each have a peak amplitude below a first specified amplitude threshold. For an example, if T-wave oversensing was not detected in at least N out of the M of the most recently detected potential VS events (e.g., four out of the seven most recently detected potential VS events, but not limited thereto), or was not detected in at least a certain percentage of the most recently detected potential VS events (e.g., 60% of the ten most recently detected potential VS events, but not limited thereto), then there can be a determination that the prevalence of T-wave oversensing is below the specified prevalence threshold. In certain embodiments, whenever an IMD determines that T-wave oversensing was not detected in at least N out of the M of the most recently detected potential VS events (e.g., four out of the seven most recently detected potential VS events), or was not detected in at least a certain percentage of the most recently detected potential VS events (e.g., 60% of the ten most recently detected potential VS events, but not limited thereto), a T-wave oversensing flag is set to false. In such an IMD, a portion of step 402 can be performed by determining whether or not the T-wave oversensing flag is set to false. If peak amplitudes associated with each of the X most recent detected potential VS events (e.g., the three most recent detected potential VS events, but not limited thereto) are below a first specified amplitude threshold (e.g., set at two times a maximum R-wave sensitivity threshold, but not limited thereto), then there can be a determination that the specified amount of most recently detected potential VS events each have a peak amplitude below the specified amplitude threshold. If the answer to the determination at step 402 is Yes, then this criterion is true and flow goes to step 310. If the answer to the determination at step 402 is No, then this criterion is false and flow goes to step 404.

At step 404 there is a determination of whether a duration of time between the detected potential VS event and an immediately preceding detected potential VS event exceeds a first specified duration threshold. The first specified duration threshold can be, e.g., three seconds, which corresponds to a cardiac pause, but is not limited thereto. If the answer to the determination at step 404 is Yes, then this criterion is true and flow goes to step 310. If the answer to the determination at step 404 is No, then this criterion is false and flow goes to step 406.

At step 406 there is a determination of whether a duration of time between the detected potential VS event and an immediately preceding detected potential VS event exceeds a second specified duration threshold (which is less than the first specified duration threshold), and a peak amplitude of the detected potential VS event is below a second specified amplitude threshold. The second specified duration threshold can be, e.g., 1.5 seconds, and the second specified amplitude threshold can be, e.g., set at two times a maximum R-wave sensitivity threshold, but are not limited thereto. If the answer to the determination at step 406 is Yes, then this criterion is true and flow goes to step 310. If the answer to the determination at step 406 is No, then this criterion is false and flow goes to step 408. The second specified amplitude threshold, can be the same as, or different than, the first specified amplitude threshold referred to above.

At step 408 there is a determination of whether VT or VF is currently being detected. Any one of various known or futured developed techniques can be used to detect VT and VF. In certain embodiments, whenever an IMD detects VT or VF it sets a tachycardia flag to true. In such an IMD, step 408 can be performed by determining whether or not the tachycardia flag is set to true. If the answer to the determination at step 408 is Yes, then this criterion is true and flow goes to step 310. If the answer to the determination at step 408 is No, then this criterion is false and flow returns to step 304.

The order of steps 402, 404, 406, and 408 can differ than the order shown and described, while still achieving the same goal. For example, the steps can occur in a reverse order, or in the order 408, 402, 406, and 404, but not limited thereto. It is also noted that additional and/or alternative types of first criteria can be used in step 308, and/or the sub-steps thereof, some example of which were discussed above.

In FIG. 4, step 314 is shows as being broken down into steps 410 and 412, which are used to determine whether various second criteria are true. At step 410 there is a determination of whether neither VT nor VF is currently being detected. If the answer to the determination at step 410 is No, then this criterion is false and flow returns to step 312. If the answer to the determination at step 410 is Yes, then this criterion is true and flow goes to step 412. As noted above, in certain embodiments, whenever an IMD detects VT or VF it sets a tachycardia flag to true. In such an IMD, step 410 can be performed by determining whether or not the tachycardia flag is set to false. At step 412 there is a determination of whether a specified amount of most recently detected potential VS events each have a peak amplitude above a third specified amplitude threshold, or have been classified as having been detected due to T-wave oversensing. In certain embodiments, as noted above, whenever an IMD determines that T-wave oversensing was not detected in at least N out of the M of the most recently detected potential VS events (e.g., four out of the seven most recently detected potential VS events, but not limited thereto), a T-wave oversensing flag is set to false. In such an IMD, step 412 can be performed by determining whether or not the T-wave oversensing flag is set to false. If the answer to the determination at step 412 is No, then this criterion is false and flow returns to step 312. If the answer to the determination at step 412 is Yes, then this criterion is true and flow goes to step 304. The order of steps 410 and 412 can be swapped, while still achieving the same goal. In other words, step 412 can be performed prior to step 410. It is also noted that additional and/or alternative types of second criteria can be used in step 314, and/or the sub-steps thereof, some example of which were discussed above.

Figure 5:
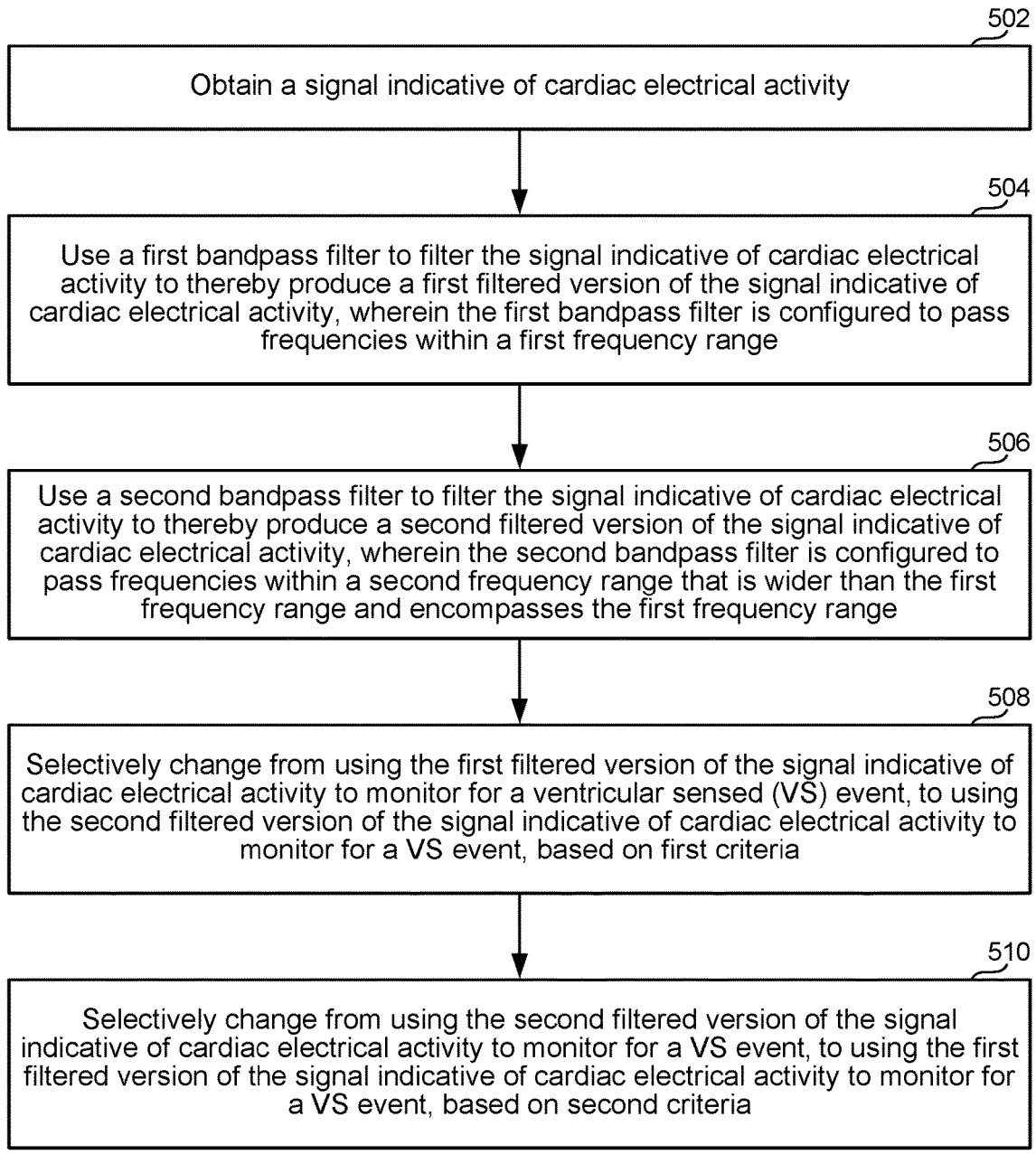
FIG. 5 is a high level flow diagram used to summarize methods according to further embodiments of the present technology.

The high level flow diagram of FIG. 5 will now be used to summarize methods according to certain embodiments of the present technology. Referring to FIG. 5, step 502 involves obtaining a signal indicative of cardiac electrical activity. The signal obtained at step 502 can be, for example, a far-field EGM or a far-field ECG, but is not limited thereto.

Still referring to FIG. 5, step 504 involves using a first bandpass filter to filter the signal indicative of cardiac electrical activity to thereby produce a first filtered version of the signal indicative of cardiac electrical activity, wherein the first bandpass filter is configured to pass frequencies within a first frequency range. Step 506 involves using a second bandpass filter to filter the signal indicative of cardiac electrical activity to thereby produce a second filtered version of the signal indicative of cardiac electrical activity, wherein the second bandpass filter is configured to pass frequencies within a second frequency range that is wider than the first frequency range and encompasses the first frequency range.

Still referring to FIG. 5, step 508 involves selectively changing from using the first filtered version of the signal indicative of cardiac electrical activity to monitor for a VS event, to using the second filtered version of the signal indicative of cardiac electrical activity to monitor for a VS event, based on first criteria. Step 510 involves selectively changing from using the second filtered version of the signal indicative of cardiac electrical activity to monitor for a VS event, to using the first filtered version of the signal indicative of cardiac electrical activity to monitor for a VS event, based on second criteria. Examples of the first and second criteria were described above, and thus, need not be described again.

Any one of various known or futured developed techniques can be used to detect T-wave oversensing, at least in part for the purpose of determining whether certain ones of the various criteria described herein are true. For an example, techniques described in U.S. patent application Ser. No. 17/153,036, filed Jan. 20, 2021, titled METHODS AND SYSTEMS FOR DISTINGUISHING OVERSENSED R-R INTERVALS FROM TRUE R-R INTERVALS, can be used. For another example, techniques described in U.S. Pat. No. 7,813,791, titled Systems and methods for employing an FFT to distinguish R-waves from T-waves using an implantable medical device, can be used. For further examples, techniques described in U.S. Pat. No. 9,597,525 titled T-wave oversensing rejection, U.S. Pat. No. 8,886,296 titled T-wave oversensing, or U.S. Pat. No. 8,942, 795 titled Implantable medical device with real time T-wave oversensing detection, can be used. These are just a few examples of techniques can be used to detect T-wave oversensing, at least in part for the purpose of determining whether certain ones of the various criteria described herein are true. Other techniques can be used to detect T-wave oversensing, while still being within the scope of the embodiments described herein.

Figure 6:
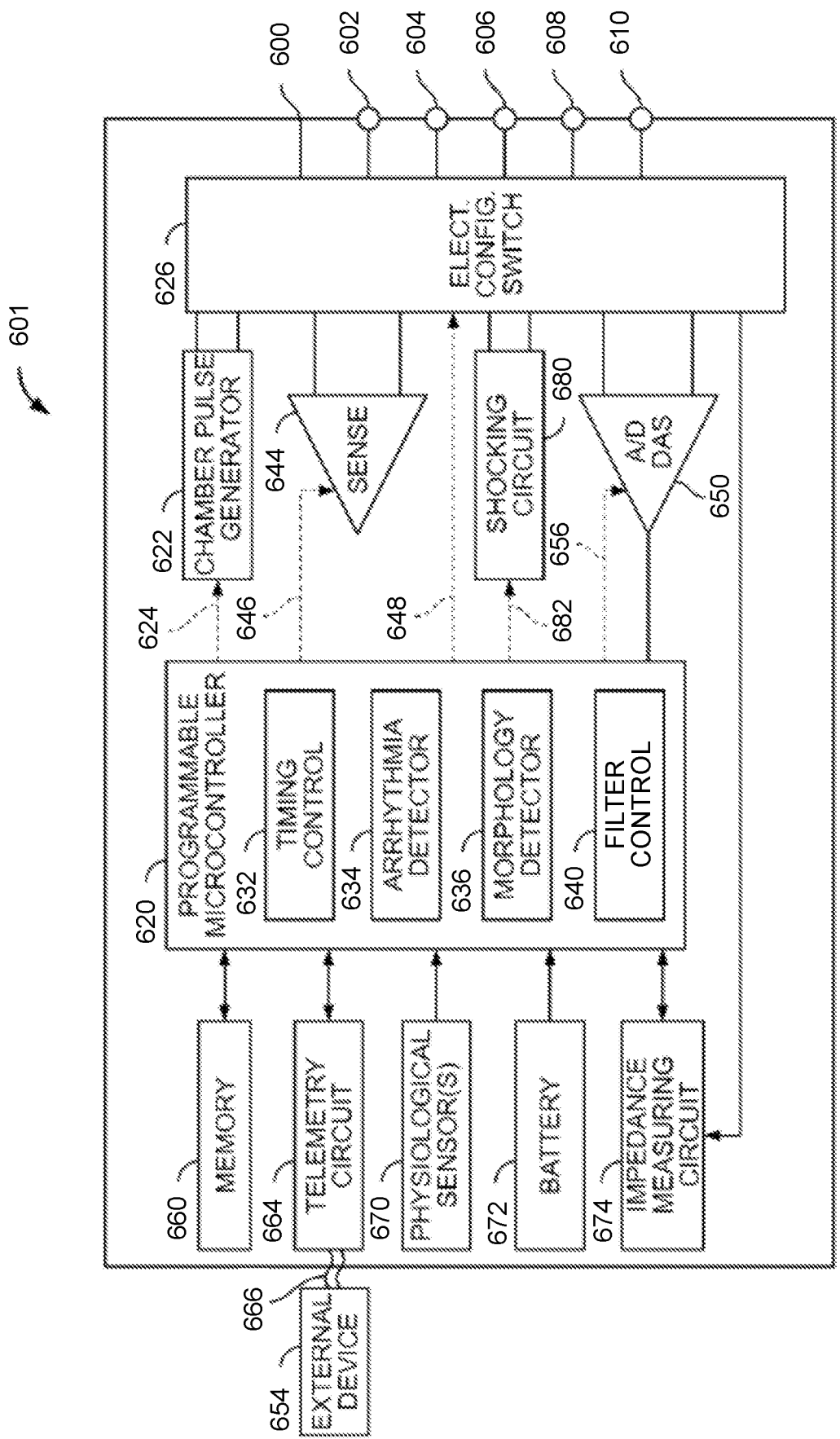
FIG. 6 shows a block diagram of one embodiment of an IMD that is implanted into a patient in accordance with certain embodiments of the present technology.

FIG. 6 shows a block diagram of one embodiment of an IMD 601 that is implanted into a patient in accordance with a certain embodiment of the present technology. The IMD 601 is one example of a device or system that can perform one of the methods described above, and/or can include the circuitry described with reference to FIGS. 1 and 2.

The IMD 601 may be implemented as a full-function biventricular pacemaker, equipped with both atrial and ventricular sensing and pacing circuitry for four chamber sensing and stimulation therapy (including both pacing and shock treatment). Optionally, the IMD 601 may provide full-function cardiac resynchronization therapy. Alternatively, the IMD 601 may be implemented with a reduced set of functions and components. For instance, the IMD may be implemented without pacing, e.g., if the IMD is an insertable cardiac monitor (ICM). The IMD 601 can be coupled to one or more leads for single chamber or multi-chamber pacing and/or sensing. Alternatively, the IMD 601 can be a leadless cardiac pacemaker (LCP) that includes electrodes located on or very close to a housing 600 of the IMD 601.

The IMD 601 has a housing 600 to hold the electronic/computing components. The housing 600 (which is often referred to as the "can", "case", "encasing", or "case electrode") may be programmably selected to act as the return electrode for certain stimulus modes. The housing 600 may further include a connector (not shown) with a plurality of terminals 602, 604, 606, 608, and 610. The terminals may be connected to electrodes that are located in various locations on the housing 600 or to electrodes located on leads. The electrodes to which the terminals 602, 604, 606, 608, and 610 are connected can also be referenced, respectively, using reference numbers 602, 604, 606, 608, and 610, and the case electrode can be referenced as case electrode 600. The IMD 601 includes a programmable microcontroller 620 that controls various operations of the IMD 601, including cardiac monitoring and/or stimulation therapy. The microcontroller 620 includes a microprocessor (or equivalent control circuitry), RAM and/or ROM memory, logic and timing circuitry, state machine circuitry, and I/O circuitry, and/or the like.

The IMD 601 further includes a pulse generator 622 that generates stimulation pulses and communication pulses for delivery by two or more electrodes coupled thereto. The pulse generator 622 is controlled by the microcontroller 620 via a control signal 624. The pulse generator 622 may be coupled to the select electrode(s) via an electrode configuration switch 626, which includes multiple switches for connecting the desired electrodes to the appropriate I/O circuits, thereby facilitating electrode programmability. The switch 626 is controlled by a control signal 628 from microcontroller 620.

In the embodiment of FIG. 6, a single pulse generator 622 is illustrated. Optionally, the IMD may include multiple pulse generators, similar to the pulse generator 622, where each pulse generator is coupled to two or more electrodes and controlled by the microcontroller 620 to deliver select stimulus pulse(s) to the corresponding two or more electrodes.

The microcontroller 620 is illustrated as including timing control circuitry 632 to control the timing of the stimulation pulses (e.g., pacing rate, atrio-ventricular (AV) delay, atrial interconduction (A-A) delay, or ventricular interconduction (V-V) delay, etc.). The timing control circuitry 632 may also be used for the timing of refractory periods, blanking intervals, noise detection windows, evoked response windows, alert intervals, marker channel timing, and so on. The microcontroller 620 also has an arrhythmia detector 634 for detecting arrhythmia conditions and a morphology detector 636. Although not shown, the microcontroller 620 may further include other dedicated circuitry and/or firmware/software components that assist in monitoring various conditions of the patient's heart and managing pacing therapies. For an example, the microcontroller can include a T-wave oversensing module that is configured to detect T-wave oversensing and keep track of the prevalence thereof.

The IMD 601 can be further equipped with a communication modem (modulator/demodulator) to enable wireless communication with the remote slave pacing unit. The modem may include one or more transmitters and two or more receivers. In one implementation, the modem may use low or high frequency modulation. As one example, modem may transmit implant-to-implant (i2i) messages and other signals through conductive communication between a pair of electrodes. Such a modem may be implemented in hardware as part of the microcontroller 620, or as software/firmware instructions programmed into and executed by the microcontroller 620. Alternatively, the modem may reside separately from the microcontroller as a standalone component.

The IMD 601 includes a sensing circuit 644 selectively coupled to two or more electrodes, that perform sensing operations, through the switch 626 to detect the presence of cardiac activity in the right chambers of the heart. The sensing circuit 644 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. The switch 626 determines the sensing polarity of the cardiac signal by selectively closing the appropriate switches. In this way, the clinician may program the sensing polarity independent of the stimulation polarity.

The output of the sensing circuit 644 is connected to the microcontroller 620 which, in turn, triggers or inhibits the pulse generator 622 in response to the presence or absence of cardiac activity. The sensing circuit 644 receives a control signal 646 from the microcontroller 620 for purposes of controlling the gain, threshold, polarization charge removal circuitry (not shown), and the timing of any blocking circuitry (not shown) coupled to the inputs of the sensing circuitry.

In the embodiment of FIG. 6, a single sensing circuit 644 is illustrated. Optionally, the IMD may include multiple sensing circuits, similar to the sensing circuit 644, where each sensing circuit is coupled to two or more electrodes and controlled by the microcontroller 620 to sense electrical activity detected at the corresponding two or more electrodes. The sensing circuit 644 may operate in a unipolar sensing configuration or in a bipolar sensing configuration.

The IMD 601 further includes an analog-to-digital (ND) data acquisition system (DAS) 650 coupled to two or more electrodes via the switch 626 to sample cardiac signals across any pair of desired electrodes. Data acquisition system 650 is configured to acquire electrogram signals, convert the raw analog data into digital data, and store the digital data for later processing and/or telemetric transmission to an external device 654 (e.g., a programmer, local transceiver, or a diagnostic system analyzer). Data acquisition system 650 is controlled by a control signal 656 from the microcontroller 620. The data acquisition system 650 can, for example, include the amplifier 112 and the ADC 114 described above in the discussion of FIGS. 1 and 2. Alternatively, the ADC 114, which was described above in the discussion of FIGS. 1 and 2, can be downstream of the sensing circuit 644, and the filters 116 can be downstream thereof, and amplifier 118 and R-wave detector 120 can be downstream thereof.

The microcontroller 620 is also shown as including a filter controller 640, which can be used to perform any of the embodiments of the present technology described above with reference to FIGS. 1-5. More specifically, the filter controller 640 can be the controller 130 described above in the discussion of FIGS. 1 and 2. The filter controller 640 can more generally be implemented using hardware, software, firmware, and/or combinations thereof. The microcontroller 620 can include a processor. The microcontroller, and/or the processor thereof, can be used to perform the methods of the present technology described herein.

The microcontroller 620 can also be used to implement the R-wave detector 120 described above in the discussion of FIGS. 1 and 2. Alternatively, the R-wave detector 120 can be implemented using circuitry that is separate from the microcontroller 120. Further, where the filters 116 (e.g., 116*a* and 116*b*; or 116*a*, 116*b* and 116*c*) described above in the discussion of FIGS. 1 and 2 are digital filters, the filters 116 can be implemented by the microcontroller 620. Alternatively, the filters 116 can be implemented in circuitry that is separate from the microcontroller 620.

The microcontroller 620 is coupled to a memory 660 by a suitable data/address bus. The programmable operating parameters used by the microcontroller 620 are stored in memory 660 and used to customize the operation of the IMD 601 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the IMD 601 may be non-invasively programmed into memory 660 through a telemetry circuit 664 in telemetric communication via a communication link 666 with an external device 654. The telemetry circuit 664 allows intracardiac electrograms and status information relating to the operation of the IMD 601 (as contained in the microcontroller 620 or memory 660) to be sent to the external device 654 through the communication link 666.

The IMD 601 can further include magnet detection circuitry (not shown), coupled to the microcontroller 620, to detect when a magnet is placed over the unit. A magnet may be used by a clinician to perform various test functions of IMD 601 and/or to signal the microcontroller 620 that the external device 654 is in place to receive or transmit data to the microcontroller 620 through the telemetry circuit 664.

The IMD 601 can further include one or more physiological sensors 670. Such sensors are commonly referred to as "rate-responsive" sensors because they are typically used to adjust pacing stimulation rates according to the exercise state of the patient. However, the physiological sensor(s) 670 may further be used to detect changes in cardiac output, changes in the physiological condition of the heart, or diurnal changes in activity (e.g., detecting sleep and wake states). Signals generated by the physiological sensor(s) 670 are passed to the microcontroller 620 for analysis. The microcontroller 620 responds by adjusting the various pacing parameters (such as rate, AV Delay, V-V Delay, etc.) at which the atrial and ventricular pacing pulses are administered. While shown as being included within the IMD 601, one or more physiological sensor(s) 670 may be external to the IMD 601, yet still be implanted within or carried by the patient. Examples of physiologic sensors include sensors that, for example, sense respiration rate, pH of blood, ventricular gradient, activity, position/posture, minute ventilation (MV), and so forth.

A battery 672 provides operating power to all of the components in the IMD 601. The battery 672 is preferably capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 672 also desirably has a predictable discharge characteristic so that elective replacement time can be detected. As one example, the IMD 601 employs lithium/silver vanadium oxide batteries.

The IMD 601 further includes an impedance measuring circuit 674, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 674 is coupled to the switch 626 so that any desired electrode may be used. In this embodiment the IMD 601 further includes a shocking circuit 680 coupled to the microcontroller 620 by a data/address bus 682.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 3 through 5. It would also be possible to reorder some of the steps shown in FIGS. 3 through 5. For another example, it is possible to change the boundaries of some of the blocks shown in FIGS. 1, 2 and 6.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. An apparatus, comprising:
   two or more electrodes;
   a sensing circuit coupleable to at least two of the electrodes to thereby sense a signal indicative of cardiac electrical activity;
   a first bandpass filter configured to pass frequencies within a first frequency range and that can be used to produce a first filtered version of the signal indicative of cardiac electrical activity;
   a second bandpass filter configured to pass frequencies within a second frequency range and that can be used to produce a second filtered version of the signal indicative of cardiac electrical activity, wherein the second frequency range is wider than the first frequency range;

an R-wave detector; and
a controller configured to cause only one of the first or second filtered versions of the signal indicative of cardiac electrical activity to be provided to the R-wave detector at a time;
the R-wave detector configured to monitor for a potential ventricular sensed (VS) event based on the only one of the first or second filtered versions of the signal indicative of cardiac electrical activity, which is caused to be provided to the R-wave detector by the controller at the time; and
the controller configured to
 determine whether one or more first criteria are satisfied, in response to a said potential VS event being detected by the R-wave detector based on the first filtered version of the signal indicative of cardiac electrical activity; and
 change from causing the first filtered version of the signal indicative of cardiac electrical activity to be provided to the R-wave detector, to causing the second filtered version of the signal indicative of cardiac electrical activity to be provided to the R-wave detector, based on results of the determination of whether the one or more first criteria are satisfied.

2. The apparatus of claim 1, wherein:
the first frequency range passed by the first bandpass filter is one of 6-25 Hz or 8-25 Hz; and
the second frequency range passed by the second bandpass filter is 3-25 Hz.

3. The apparatus of claim 1, wherein the controller is configured to:
determine whether one or more second criteria are satisfied, in response to a said potential VS event being detected by the R-wave detector based on the second filtered version of the signal indicative of cardiac electrical activity; and
change from causing the second filtered version of the signal indicative of cardiac electrical activity to be provided to the R-wave detector, to causing the first filtered version of the signal indicative of cardiac electrical activity to be provided to the R-wave detector, based on results of the determination of whether the one or more second criteria are satisfied.

4. The apparatus of claim 3, wherein the one or more first criteria are configured to at least one of:
detect R-wave undersensing; and
reduce a chance of R-wave undersensing during an episode of at least one of ventricular tachycardiac (VT) or ventricular fibrillation (VF).

5. The apparatus of claim 3, wherein the one or more first criteria include:
(i) a prevalence of T-wave oversensing is below a first specified prevalence threshold, and a specified amount of most recently detected potential VS events each have a peak amplitude below a first specified amplitude threshold;
(ii) a duration of time between the detected potential VS event and an immediately preceding detected potential VS event exceeds a first specified duration threshold; and
(iii) a duration of time between the detected potential VS event and an immediately preceding detected potential VS event exceeds a second specified duration threshold, which is less than the first specified duration threshold, and a peak amplitude of the detected potential VS event is below a second specified amplitude threshold; and
wherein the controller changes from causing the first filtered version of the signal indicative of cardiac electrical activity to be provided to the R-wave detector, to causing the second filtered version of the signal indicative of cardiac electrical activity to be provided to the R-wave detector, in response to the controller determining that at least one of the criteria (i), (ii), or (iii) is true.

6. The apparatus of claim 4, wherein the one or more first criteria includes:
(iv) at least one of ventricular tachycardiac (VT) or ventricular fibrillation (VF) is (iv) currently being detected; and
wherein the controller changes from causing the first filtered version of the signal indicative of cardiac electrical activity to be provided to the R-wave detector, to causing the second filtered version of the signal indicative of cardiac electrical activity to be provided to the R-wave detector, in response to the controller determining that the criterion (iv) is true.

7. The apparatus of claim 3, wherein the one or more second criteria are used by the controller to reduce a chance of T-wave oversensing causing a false detection of ventricular tachycardiac (VT) or ventricular fibrillation (VF).

8. The apparatus of claim 1, wherein;
the first and second filtered versions of the signal indicative of cardiac electrical activity are produced in parallel by passing the signal indicative of cardiac electrical activity through the first bandpass filter included within a first channel, and also separately passing the signal indicative of cardiac electrical activity through the second bandpass filter included in a second channel; and
the controller controls whether the first channel or the second channel is coupled to the R-wave detector.

9. The apparatus of claim 1, wherein:
the controller is configured to make an additional determination whether the one or more first criteria are satisfied each time the R-wave detector detects an additional potential VS event based on the first filtered version of the signal indicative of cardiac electrical activity, and to change from causing the first filtered version of the signal indicative of cardiac electrical activity to causing the second filtered version of the signal indicative of cardiac electrical activity to be provided to the R-wave detector, based on results of the additional determination of whether the one or more first criteria are satisfied.

10. The apparatus of claim 3, wherein:
the controller is configured to make an additional determination whether the one or more first criteria are satisfied each time the R-wave detector detects an additional potential VS event based on the first filtered version of the signal indicative of cardiac electrical activity, and to change from causing the first filtered version of the signal indicative of cardiac electrical activity to causing the second filtered version of the signal indicative of cardiac electrical activity to be provided to the R-wave detector, based on results of the additional determination of whether the one or more first criteria are satisfied; and
the controller is configured to make an additional determination whether the one or more second criteria are satisfied each time the R-wave detector detects an additional potential VS event based on the second filtered version of the signal indicative of cardiac electrical activity, and to change from causing the second filtered version of the signal indicative of cardiac electrical activity to causing the first filtered version of the signal indicative of cardiac electrical activity to be provided to the R-wave detector, based on results of the additional determination of whether the one or more second criteria are satisfied.

11. An apparatus, comprising:

two or more electrodes;

a sensing circuit coupleable to at least two of the electrodes to thereby sense a signal indicative of cardiac electrical activity;

a first bandpass filter configured to pass frequencies within a first frequency range and that can be used to produce a first filtered version of the signal indicative of cardiac electrical activity;

a second bandpass filter configured to pass frequencies within a second frequency range and that can be used to produce a second filtered version of the signal indicative of cardiac electrical activity, wherein the second frequency range is wider than the first frequency range;

an R-wave detector; and a controller configured to cause only one of the first or second filtered versions of the signal indicative of cardiac electrical activity to be provided to the R-wave detector at a time;

the R-wave detector configured to monitor for a potential ventricular sensed (VS) event based on the only one of the first or second filtered versions of the signal indicative of cardiac electrical activity, which is caused to be provided to the R-wave detector by the controller at the time; and the controller configured to determine whether one or more first criteria are satisfied, in response to a said potential VS event being detected by the R-wave detector based on the first filtered version of the signal indicative of cardiac electrical activity; and change from causing the first filtered version of the signal indicative of cardiac electrical activity to be provided to the R-wave detector, to causing the second filtered version of the signal indicative of cardiac electrical activity to be provided to the R-wave detector, based on results of the determination of whether the one or more first criteria are satisfied;

determine whether one or more second criteria are satisfied, in response to a said potential VS event being detected by the R-wave detector based on the second filtered version of the signal indicative of cardiac electrical activity; and change from causing the second filtered version of the signal indicative of cardiac electrical activity to be provided to the R-wave detector, to causing the first filtered version of the signal indicative of cardiac electrical activity to be provided to the R-wave detector, based on results of the determination of whether the one or more second criteria are satisfied;

wherein the one or more second criteria include:

(i) neither ventricular tachycardiac (VT) nor ventricular fibrillation (VF) is currently being detected; and (ii) a specified amount of most recently detected potential VS events each have a peak amplitude above a further specified amplitude threshold, or have been classified as having been detected due to T-wave oversensing; and wherein the controller changes from causing the second filtered version of the signal indicative of cardiac electrical activity to be provided to the R-wave detector, to causing the first filtered version of the signal indicative of cardiac electrical activity to be provided to the R-wave detector, in response to the controller determining that both criteria (i) and (ii) are true.

* * * * *